US010485967B2

(12) United States Patent
Sameti et al.

(10) Patent No.: US 10,485,967 B2
(45) Date of Patent: Nov. 26, 2019

(54) SYSTEM FOR THE TRANSDERMAL DELIVERY OF ACTIVE INGREDIENT (71) Applicant: LTS Lohmann Therapie-Systeme AG, Andernach (DE)

(72) Inventors: Mohammad Sameti, Bonn (DE); Ronald Hackbarth, Koblenz (DE); Klaus Schumann, Neuwied (DE); Christoph Schmitz, Rheinbrohl (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 123 days.

(21) Appl. No.: 15/105,821

(22) PCT Filed: Dec. 17, 2014

(86) PCT No.: PCT/EP2014/003399
§ 371 (c)(1),
(2) Date: Jun. 17, 2016

(87) PCT Pub. No.: WO2015/090583
PCT Pub. Date: Jun. 25, 2015

(65) Prior Publication Data
US 2016/0303361 A1 Oct. 20, 2016

(30) Foreign Application Priority Data

Dec. 20, 2013 (EP) .................................... 13199189

(51) Int. Cl.
*A61N 1/04* (2006.01)
*A61K 31/27* (2006.01)
(Continued)

(52) U.S. Cl.
CPC ............ *A61N 1/0448* (2013.01); *A61K 31/27* (2013.01); *A61K 31/4468* (2013.01);
(Continued)

(58) Field of Classification Search
CPC ................. A61N 1/0448; A61N 1/303; A61M 2037/0007
See application file for complete search history.

(56) References Cited

U.S. PATENT DOCUMENTS 222,276 A   12/1879 Hunter
486,902 A   11/1892 Shults
(Continued)

FOREIGN PATENT DOCUMENTS

JP   H11-192313 A   7/1999
JP   2014-068847 A   4/2014
(Continued)

OTHER PUBLICATIONS

Luzardo-Alvarez, A., et al., "Iontophoretic Delivery of Ropinirole HCI: Effect of Current Density and Vehicle Formulation," Proceedings of the International Symposium on Controlled release of Bioactive Materials, Jul. 2000, 27th Ed., pp. 159-160, Controlled Release Society, Inc.

*Primary Examiner* — Bradley J Osinski
(74) *Attorney, Agent, or Firm* — ProPat, LLC; Vinisha Joshi (57) ABSTRACT The invention relates to a transdermal therapeutic system (TTS) for delivering pharmaceutical active ingredients. The TTS includes a cover layer and at least one active-ingredient-containing carrier material. At least one retaining element is located between the active-ingredient-containing carrier material and the cover layer, with the retaining element fixing the active-ingredient-containing carrier material onto the cover layer. The invention further relates to a method for fastening an active-ingredient-containing carrier material to a cover layer of a TTS in the presence of hook-and-loop strip segments and the use of a hook-and-
(Continued)

loop strip in transdermal or iontophoretic administration of pharmaceutical or therapeutic active ingredients to patients.

1 Claim, 3 Drawing Sheets

(51) Int. Cl.

| | |
|---|---|
| *A61K 31/4468* | (2006.01) |
| *A61K 31/485* | (2006.01) |
| *A61K 31/55* | (2006.01) |
| *A61K 38/22* | (2006.01) |
| *A61K 38/27* | (2006.01) |
| *A61K 38/28* | (2006.01) |
| *A61K 38/36* | (2006.01) |
| *A61M 37/00* | (2006.01) |
| *A61N 1/30* | (2006.01) |

(52) U.S. Cl.
CPC ............ *A61K 31/485* (2013.01); *A61K 31/55* (2013.01); *A61K 38/2271* (2013.01); *A61K 38/27* (2013.01); *A61K 38/28* (2013.01); *A61K 38/36* (2013.01); *A61M 37/00* (2013.01); *A61N 1/0428* (2013.01); *A61N 1/0436* (2013.01); *A61N 1/303* (2013.01); *A61M 2037/0007* (2013.01); *A61M 2207/00* (2013.01)

(56) References Cited

U.S. PATENT DOCUMENTS

| | | | |
|---|---|---|---|
| 5,558,633 A | 9/1996 | Phipps et al. | |
| 5,645,526 A * | 7/1997 | Flower | A61N 1/303 |
| | | | 604/20 |
| 5,685,837 A | 11/1997 | Horstmann | |
| 5,817,044 A | 10/1998 | Evers et al. | |
| 6,745,071 B1 | 6/2004 | Anderson et al. | |
| 7,127,285 B2 * | 10/2006 | Henley | A61N 1/044 |
| | | | 604/20 |
| 8,224,435 B2 * | 7/2012 | Gyory | A61N 1/0448 |
| | | | 604/20 |
| 2002/0019652 A1 * | 2/2002 | Da Silva | A61N 1/0456 |
| | | | 607/72 |
| 2010/0076387 A1 | 3/2010 | Weimann et al. | |
| 2010/0137779 A1 * | 6/2010 | Seitz | A61N 1/30 |
| | | | 604/20 |

FOREIGN PATENT DOCUMENTS

| | | |
|---|---|---|
| WO | WO 2010/027468 A1 | 3/2010 |
| WO | WO 2012/071175 A1 | 5/2012 |

\* cited by examiner

SYSTEM FOR THE TRANSDERMAL DELIVERY OF ACTIVE INGREDIENT

CROSS-REFERENCE TO RELATED APPLICATIONS

This application is being filed under 35 U.S.C. § 371 as a National Stage Application of pending International Application No. PCT/EP2014/003399 filed Dec. 17, 2014, which claims priority to parent application German Patent Application No. 13199189.5, filed Dec. 20, 2013. Both International Application No. PCT/EP2014/003399 and German Patent Application No. 13199189.5 are hereby incorporated by reference herein in their entirety.

FIELD OF THE INVENTION

The present invention relates to a novel system for the delivery of pharmaceutical actives in a therapeutically effective amount to the organism.

The present invention preferably relates to a simple-to-handle system for the transdermal delivery of a therapeutically effective amount of a pharmaceutical active dissolved in a liquid, more preferably the transdermal delivery of a cationic active via iontophoresis.

BACKGROUND OF THE INVENTION

The transdermal route of parenteral administration offers numerous advantages over other administration routes. Methods and systems to administer drugs through the skin are widely known in the field of pharmacy. Transdermal administration typically utilizes passive transdermal systems (e.g., Transdermal Therapeutic Systems, TTS), which supply the organism with defined amounts of pharmaceutical actives via diffusion through the skin.

Specifically the transdermal transport of actives dissolved in a liquid is problematical in that a gel or a sponge cloth or nonwoven carrier material containing the active has to be kept separate from the backing layer, together with which the active in the TTS is fixed to the skin, since prolonged storage stability is otherwise not ensured or since the active may have to be kept cooled or since it may be sensitive to oxidation. The user of a medicated patch then has to transfer the active-containing carrier material, having moved it from its usually sealed and hence liquid-impervious package by removing the closure film, to the backing layer of a transdermal therapeutic system (TTS) and fix it thereon. All the while, however, because of the risk of germ transfer, the user should ideally not touch the active-containing carrier material with his or her fingers and should ideally also not use any additional aids to effect the transfer.

The usual procedure is therefore to place the TTS backing layer face down onto the upwardly opened package of active-containing carrier material and press the carrier material against the TTS backing layer. When the TTS is thereafter removed again from the opened package, the active-containing carrier material is left adhering to the TTS backing layer, combining therewith to form the TTS in the actual sense, but this does not always happen reliably. Oftentimes or at least occasionally, the carrier material with the active is simply left behind in the package.

One place where this problem occurs is with the method of iontophoresis, which is deployed when passive transdermal drug delivery is but very inefficient for certain types of drugs. Ionized medicaments in particular are often unable to passively pass through the skin in a therapeutically effective amount.

The process of iontophoresis was originally described by LeDuc in 1908 and even earlier in US-222,276 (1879) and US-486,902 (1892). Iontophoresis has since found commercial use in the transdermal delivery of ionically charged therapeutically active molecules such as pilocarpine, lidocaine, dexamethasone, lidocaine and fentanyl.

Iontophoresis in general is a delivery method based on the fundamental principle that the application of electrical current makes available external energy to increase the ability of a drug to permeate through the membranes of the skin by improving the passage of active-ingredient ions through the skin.

When ions bearing a positive charge (cationic actives, for example) are placed into or underneath the anode of an iontophoretic system, the application of a current will cause an impulse to be exerted on these ions which moves them away from the anode in the direction of the electrical field toward the cathode, arranged in the immediate vicinity of the skin. During this process, the transportation of the cationic drug through the skin is improved or facilitated.

Iontophoresis can be carried out with various forms of active pharmaceutical ingredients, most favorably with those which have an electrical charge and which, in an electrical field, thus develop the ability to cross barriers (e.g., the skin).

A typical iontophoretic drug delivery system comprises an electrolytic electrical system composed of an anode and a cathode, which are placed on different—preferably adjacent—skin areas of a patient, each electrode being connected via a wire to an external power supply. In general, this is a microprocessor-controlled electrical instrument. Such types of devices are known, including systems of extremely simple design (e.g., U.S. Pat. No. 5,685,837 or 6,745,071) or else more complex systems of which a person skilled in the art has in-principle knowledge. Iontophoretic transdermal systems for lidocaine and fentanyl have already been successfully launched in the U.S. A very particularly detailed description of a system for delivering drugs by means of iontophoresis is found in WO 2012/071175.

U.S. Pat. No. 5,558,633 relates that iontophoresis devices are particularly suitable for the delivery of medicaments from a liquid or from gelled aqueous formulations. However, in such devices, the iontophoretic administration of pharmaceutical actives can be greatly impaired by the presence of "background" electrolytes (see for instance Luzardo-Alvarez, A., et al., Proceedings of the International Symposium on Controlled Release of bioactive Materials (2000), 27th Ed., pp. 159 to 160). Regarding the design of iontophoretic devices, moreover, there is a want of pharmaceutical gels or liquids which do not themselves have a disruptive effect as "background" counterions.

Various still existing deficiencies notwithstanding, iontophoresis has proved useful as a delivery method in all those cases where a conventional TTS does not suffice to ensure the rapid administration of a therapeutically effective dose of such an active ingredient. However, there is the inherent risk with iontophoresis that side-effects such as skin irritation, skin reddening, burning or else skin necrosis can occur in particular on increasing the current strength or on practicing the iontophoretic treatment for a prolonged period. On the other hand, an increase in the current strength can be perfectly desirable for the administration of higher doses of therapeutic active, since the number of ions transported is directly proportional to the level of current flow per unit time.

The problem addressed by the present invention in view of the above was therefore that of providing a method whereby an active-containing carrier material can be reliably removed from its pack and fixed to the TTS backing layer for the purposes of subsequent application—whether with or without augmentation by iontophoresis—without this requiring the active-containing carrier material to be touched by hand or an additional aid being needed to effect the transfer.

US 2002/0019652 A1 discloses a patch for transcurtaneous electrical nerve stimulation (TENS). The TENS method is a non-invasive pain management method which in principle eschews pharmaceutical actives. In one embodiment, the patch comprises a reusable upper part which contains an electronics module and switches to turn the power supply on and off and adjust the current strength. The lower part is subdivided into three sections arranged side by side. The two outer sections serve as plus and minus electrodes and are intended for direct contact with the skin, while the center section consists with preference of sterile gauze material. The gauze material may contain an active. In a particular embodiment, the upper part as depicted in FIG. 3 contains a layer (70) of a magnetic polymer. The lower part (40) likewise contains a layer (86) of magnetic polymer at the upper side, as depicted in FIG. 4. The magnetic layers of the two parts can then adhere to each other. According to para [0023], the sterile gauze is absorbent in the region (80). It is thus supposed to absorb wound exudate or the like. In a further embodiment, the upper and lower parts are joined together by a hook and loop fastener (Velcro). The magnetic layer (70) of the upper part is then replaced by one half of the hook and loop fastener, and the magnetic layer (86) of the lower part by the other half.

WO 2012/071175 A1 discloses an iontophoretic patch in a two-part protective sleeve. The electrodes (22) and (24) are separated from the active-containing carrier material (42) or, respectively, (44) by a barrier film (52) or, respectively, (54). The ends (52a) and (54a) of the film project out of the protective sleeve (60a) and (60b). The barrier film is pulled out before use. Mechanical pressure on the protective sleeve puts the electrodes into direct contact with the active-containing carrier material. Before applying the iontophoretic patch, the protective sleeve is removed (see FIG. 5A to 5F). The separation of the electrodes from the active-containing carrier material is intended to extend the shelf life of the patch.

SUMMARY OF ADVANTAGEOUS EMBODIMENTS OF THE INVENTION

This problem is solved by a TTS of the incipitly classified type, comprising a backing layer and at least one active-containing carrier material, wherein at least one retaining element between the active-containing carrier material and the backing layer secures the active-containing carrier material to the backing layer.

In a preferred embodiment of the present invention, the retaining element is configured as an elongately shaped segment of a hook and loop tape.

DETAILED DESCRIPTION OF ADVANTAGEOUS EMBODIMENTS OF THE INVENTION

The reference to a hook and loop tape in the present application is to be understood as meaning a textile, arbitrarily often releasable fastening means based on the principle of burs. The bionic implementation consists, typically, of two woven strips of fiber, one displaying flexible barbed hooks or mushroom heads, the other by contrast loops. Pressed together they combine to form a more or less resistant, but at any rate reversible high-speed fastener. Woven hook and loop tapes consist of polyamide, polyester or polyolefin fibers. The hooks are incorporated in the hook tapes during weaving or later. Hook and loop tapes and touch fasteners may also be rendered self-adhesive on the reverse side by coating with pressure-sensitive adhesives.

In the present invention, the hook and loop tape disposed on the backing layer of the TTS forms the hook side, while the active-containing carrier material assumes the function of the loop side. By pressing the retaining element which is mounted on the backing layer of the TTS onto the upper side of the package containing the active-containing carrier material and upwardly opened by prior removal of the closure film, the present invention causes the hook and loop tape to become hookingly engaged with the carrier material, to adhere to the retaining element of the TTS as the TTS is detached from the package and not to be left behind in the package when the latter is thereafter removed again.

In general, the active-containing carrier material is situated in the package which is opened by removal of the closure film immediately before the transfer of the carrier material plus active to the backing layer of the TTS.

The active-containing carrier material is liquid saturated and as such adheres to the packaging film. To release the carrier material from the packaging film therefore requires a force ($x_1$). If, now, the carrier material is to be transferred to the TTS without additional aids such as, for example, fingers or gripping elements being used for this, then the TTS is laid flat onto the carrier material and pressed down. This causes the liquid-saturated carrier material to additionally adhere to the pressed-down TTS (polymeric film/polyester film). However, the adhering forces to the TTS (=$F_{rts}$) are similar to the adhering forces to the packaging (=$F_{pack}$). On removing the TTS again after it has been pressed down, the magnitude of the two adhering forces decides whether the active-containing carrier material remains adhering to the TTS or alternatively to the package. Unless the adhering force to the TTS ($F_{rts}$) is significantly greater than the adhering force to the packaging film ($F_{pack}$), there is a risk that the liquid-saturated carrier material remains behind in the package and not, as desired, adhering to the TTS.

In order for a successful transfer of the active-containing carrier material from the packaging film to the TTS to take place, the adhering forces have to be changed such that they are significantly different:

$$F_{tts} >> F_{pack}$$

The adhering force of the active-containing carrier material to the packaging film can scarcely be reduced. Even anti-stick coatings reduce this adhering force but insignificantly owing to the viscosity of the liquid. Even a profiling of the surface does not elicit any change in the adhering forces, since the liquid fills the surface profiling and displaces air inclusions.

Increasing the adhering forces to the TTS ($F_{tts}$) would therefore be a solution to the problem of reliably ensuring the transfer process. The invention deploys a hook and loop tape to increase the adhering forces to the TTS ($F_{tts}$). Owing to the hook and loop tape, the adhering forces of the active-containing carrier material ($F_{tts}$) increase significantly. This is because hook and loop tapes are even able to function in a moist state. As the active-containing carrier material is pressed against the hook and loop tape, the fibers of the carrier material become hookingly engaged with the hooks of the hook and loop tape. So the hook and loop tape increases the adhering force ($F_{tts}$) significantly even in a moist environment, guaranteeing the transfer of the liquid-saturated carrier material from the package to the backing layer of the TTS.

Backing layer refers for the purposes of the present application to a substantially self-supporting sheet body which covers that part of the skin where the transdermal delivery of pharmaceutic active to the organism takes place. If the TTS is not attached to the skin via a pressure-sensitively adhesive overplaster, then the backing layer conveniently also has the function to secure the system to the skin, this being accomplished by a uniformly or patternedly pressure-sensitively adhesive implementation of that side of the backing layer which faces the skin, wherein the area(s) for the active-containing carrier material(s) are free from pressure-sensitive adhesive at least.

In a further embodiment of the invention, the backing layer is an occlusive backing layer. An occlusive backing layer is specifically a barrier layer for liquids and water vapor, preventing liquid or water vapor escaping to the outside through the backing layer, which would cause the system to dry out if the pharmaceutical active to be delivered is liquid or dissolved in a liquid. The occlusive backing layer in the present invention may consist of a self-supported film of a plastic such as polyethylene or polypropylene or polyester or polyurethane or polyamide, the essential property of which is that it constitutes a sufficiently reliable blocker to water, water vapor or water-mixed organic solvents. Suitable self-supported films of the plastics referred to have a thickness in the range from 5 to 300 μm, preferably from 10 to 200 μm, more preferably from 12 to 150 μm.

The occlusive backing layer may additionally further contain or be bonded to a non-occlusive carrier layer for reinforcement. Said non-occlusive carrier layer may suitably be a woven textile fabric or a fibrous nonwoven web or a felt material or some other cellulosic material. The bond between the non-occlusive carrier layer and the occlusive backing layer may be established by lamination under pressure or by extrusion or by bonding with a suitable adhesive. Suitable adhesives may consist of polyisoprene or polyisobutylene or polyacrylic esters or else of polysiloxane copolymers.

A self-adhesive layer may also be provided to the occlusive backing layer at its underside, i.e., the side facing the skin. The aforementioned adhesives, preferably acrylic adhesives, are useful as self-adhesive materials.

In a further embodiment, the active-containing carrier material is a hydrogel or a carrier material saturated with liquid or dusted with pulverulent active. A liquid in the present invention may comprehend a solution of an active in a solvent, preferably an aqueous solvent, or else, alternatively, a dispersion or emulsion of active in a suitable dispersing or emulsifying medium. By way of carrier materials, fibrous nonwoven web type materials or woven textile materials or knitted fabrics not produced by weft knitting with independently-movable needles or sponge-shaped materials are used with advantage or else, optionally, gel-forming polymers.

In a preferred embodiment of the present invention, the shape of the elongately shaped hook and loop tape matches the shape of the active-containing carrier material. When the active-containing carrier material has a rectangular shape, the length of the elongatedly shaped hook and loop tape preferably corresponds to the length of one of the sides of the rectangularly shaped active-containing carrier material. When the active-containing carrier material has a round or oval shape, the shape of the elongatedly shaped hook and loop tape is preferably that of an arcuate circular segment with a radius corresponding to the radius of the round or oval active-containing carrier material.

Hook and loop tapes suitable for the purposes of the present invention are self-adhesive, i.e., they adhere with their self-adhesive reverse side to the backing layer. But it is also possible for a suitable adhesive, for example an acrylic adhesive or a two-component adhesive or a hot-melt adhesive, to fasten a hook and loop tape to the backing layer.

The width of the elongatedly shaped hook and loop tape may vary between wide limits. The hook and loop tape need not cover the entire area whereover the active-containing carrier material in the TTS extends, it being instead sufficient for the elongatedly shaped hook and loop tape to cover only a or one part of the area irrespective of the geometry of the active-containing carrier material. It is also possible in this context for the hook and loop tape to be situated only in the side edge near regions or for it to be configured as a circumferential strip having a width in the range from 2 to 15 mm, preferably from 3 to 10 mm.

The present invention may also comprise two or more hook and loop tapes arranged, for example, on opposite sides of the area whereto the active-containing carrier material is or is to be fastened to the TTS.

The invention also provides a method of attaching an active-containing carrier material to a TTS backing layer in the presence of hook and loop tape segments. This involves approximating the active-containing carrier material in a package upwardly opened by a closure film being removed beforehand to the occlusive backing layer and the hook and loop tape segments disposed thereon. Then, the package is pressed together with the active-containing carrier material present therein against the hook and loop tape segments on the occlusive backing layer. Thereafter, the package can be released and removed, leaving the active-containing carrier material secured to the hook and loop tape segments and to the occlusive backing layer.

The invention further provides the method of using a hook and loop tape as a constituent part of a transdermal therapeutic system (TTS) or as a constituent part of an iontophoretic transdermal therapeutic system.

The invention further comprehends the method of using a hook and loop tape in a method for transdermal or iontophoretic administration of cationic actives to patients in need of treatment with such actives.

The system of the present invention is particularly useful specifically in connection with therapeutic actives having a cationic structure, in particular actives having amino or imino groups in their molecule.

The present invention is accordingly suitable for the transdermal, specifically the iontophoretic, administration of analgesics such as fentanyl or morphine, antiemetics such as granisetron or other central nervous system drugs such as rivastigmine or galantamine.

When the system of the present invention is used for transdermal administration of such actives, the liquid-saturated carrier material serves as a matrix or reservoir wherefrom the cationic actives are delivered to the skin and then pass through the skin either passively or with iontophoretic assistance.

Actives having a cationic structure are generally actives which are in the form of positively charged ions (cations) or which are capable of forming positively charged ions in aqueous media. Many biologically active agents for example have functional groups which readily dissociate in an aqueous medium into a positively charged ion and a counterion, examples being soluble salts of basic actives.

The term "actives" comprehends specifically therapeutically active agents, pharmacologically active agents or other agents having advantageous effects when administered to a human being or to an animal.

The term "actives" in general designates pharmaceutical actives or drugs, i.e., therapeutic actives. The expression "actives" further also comprehends agents for use in veterinary medicine.

The present invention is particularly suitable for the transdermal, specifically the iontophoretic, administration of actives such as
- opioid agonists, including analgesics such as fentanyl, sufentanyl, morphine, morphine derivatives such as codeine or such as heroin, dihydrocodeine, hydromorphine, oxycodone, hydrocodone, pethidine, loperamide, diphenoxylate, methadone, tramadol or tilidine;
- opioid antagonists such as naloxone, naltrexone;
- mixed opiate agonists/antagonists, such as buprenorphine, pentazocine, nalbuphine;
- antiemitics including 5-HT$_3$ receptor antagonists such as granisetron, lerisetron, ondansetron, dolasetron, metoclopramide and also antidopaminergic medicaments such as domperidone, and also HI receptor antagonists such as, for example, promethazine or meclozine and also muscarine antagonists such as scopolamine;
- drug compounds which act on the central nervous system, such as rivastigmine, galantamine, tacrine, donepezil, and also pramipexole, adrenaline, dopamine, ropinirole, nicotine, fluphenazine, chlorpromazine, benzodiazepines, monoamine reuptake inhibitors such as amitriptyline, antidepressives such as mianserine;
- alkaloids such as ergotamine, dihydroergotamine, methysergide or lisuride, belladonna alkaloids;
- peptides, in particular peptide hormones such as insulin and oxytocin or blood coagulation factors and growth hormones;
- cationically active indole compounds such as N-dimethyltryptamine, sumatriptan or psilocine;
- local anesthetics such as lidocaine, buprivacaine, articaine, procaine;
- gastrointestinally active therapeutics, such as carnitine chloride or metoclopramide;
- muscle relaxants such as vancuronium bromide;
- antibiotics such as tetracycline, tetracycline-based preparations, kanamycine, kanamycine-based preparations, gentamycine, gentamycine-based preparations or quinine;
- anorexics such as fenfluramine or ephedrine;
- antidiabetics such as metformin;
- inhibitors of thrombocyte aggregation, e.g., ticlopidine or clopidogrel;
- antiarrhythmics such as quinidine or lidocaine;
- cardiac or cardiovascular agents such as dopamine, noradrenaline, methoxamine, adrenaline, verapamil, diltiazem, propranolol, clonidine, tolazoline;
- sympathomimetics such as salbutamol or terbutaline;
- antihistamines such as clemastine, cetirizine or chlorphenoxamine.

In one preferred embodiment, the active comes from the group of cationic indole compounds, particularly from the group of cationic indole compounds, N-dimethyltryptamine and psilocine, this group also comprehending the pharmaceutically suitable salts of these cationically active indole compounds.

The aforementioned cationic actives can also be present in the form of pharmaceutically suitable salts. Examples of pharmaceutically suitable salts include chloride, bromide, iodide, sulfur, phosphate, lactate, citrate, tartrate, salicylate, succinate, maleate, gluconate, mesylate, laurate, dodecylate, myristate, palmitates and stearate salts, but are not limited to these.

The intensity of the current during iontophoresis should ideally not exceed a value of 600 µA/cm$^2$ so as to avoid burning the skin or a burning sensation on the skin. The starting voltage is generally in the range from 0.5 to 10 V, depending on the resistance between the two electrodes and the in-between region of the skin, which may normally be 50 kΩ or more.

In a further embodiment, the liquid-saturated carrier material contains the cationic active or a salt thereof in an amount from 0.1 to 20 wt %, preferably from 0.2 to 10 wt %, more preferably from 2 to 10 wt %, most preferably from 3 to 5 wt %, based on the overall weight of liquid in the carrier material.

The liquid in the liquid-saturated carrier material of the present invention is preferably water or an aqueous solvent mixture. The proportion of water in the solvent mixture is preferably at least 15 wt %, more preferably at least 40 wt %, based on the overall weight of liquid.

In a further embodiment of the invention, the water content or the proportion of the solvent mixture is in the range from 80 to 99 wt %.

The term "aqueous solvent mixture" comprehends in general liquid mixtures which contain water and at least one further solvent which is generally a polar water-miscible organic solvent, e.g., an alcohol such as ethanol, isopropanol or glycerol.

The present invention also comprehends applications where a cationic active is employed in combination with at least one further active which is selected from the group consisting of active agents having a neutral charge and which may even also comprehend anionic actives.

The system of the present invention generally employs actives capable of passing through the skin by passive diffusion or suitable for iontophoretic permeation of the skin.

In a further embodiment, the liquid-saturated carrier material may be a hydrogel composition, in which case additionally gel-forming polymers which may be selected from the group consisting of polyacrylates and cellulose derivatives, such as hydroxypropylmethylcellulose, hydroxypropylcellulose or hydroxyethylcellulose, are present. The use of hydrogel preparations in iontophoresis is particularly advantageous because, in this case, the ionic strength is adjustable by varying the proportion of water within the hydrogel. It is thus an easy matter to adjust the ionic strength in order to optimize the efficacy of the iontophoretic process in any one specific case.

In a further embodiment, the liquid in the liquid-saturated carrier material has a pH in the range from 3 to 8, preferably from 5.5 to 7 more preferably of about 6.

It is generally preferable to establish a pH that does not differ significantly from the skin pH when the TTS is applied to the skin. In a further embodiment, the skin pH changes by ±4.0 or less, approximately ±3.5 or less, approximately ±3.0 or less, approximately ±2.5 or less, approximately ±2.0 or less, about ±1.5 or less, approximately ±1.0 or less, or about ±0.5 or less. Substances and buffers to adjust or establish the pH are known to a person skilled in the art.

The liquid-saturated carrier material may optionally contain further additives, in which case the additives may be selected from the group of solubilizers, skin penetration enhancers, preservatives and antimicrobial agents.

In this context, the term "solubility improvers" is to be understood as meaning in general compounds capable of contributing to enhancing the solubility of the cationically active agent in the liquid. This is attainable either by modulating the possible interactions between the cationic active and the other components present in the liquid, or by the additional incorporation of suitable auxiliary materials.

Alternatively, solubility is attainable for the active by altering the crystal form. Examples of solubilizers include water, diols, such as propylene glycol and glycerol, monoalcohols such as ethanol, propanol and higher alcohols, dimethyl sulfoxide (DMSO), dimethylformamide, N,N-dimethylacetamide, N-substituted alkylazacycloalkyl-2-ones.

The term "skin permeation enhancers" further comprehends in particular compounds which contain an increase in the permeability of the skin for an active, in particular for a cationic active. Owing to this enhancement in skin perviousness, the rate at which the active penetrates through the skin and into the blood circulation increases.

Examples of permeation enhancers include dimethyl sulfoxide (DMSO), N,N-dimethylacetamide (DMA), decyl methyl sulfoxide (C10 MSO), polyethylene glycol monolaurate (PEGML), propylene glycol (PG), propylene glycol monolaurate (PGML), glycerol monolaurate (GML), lecithin, the 1-substituted alkylazacycloalkyl-2-ones, in particular indodecylcylazacycloheptan-2-one, alcohols and the like.

The permeation enhancer may also be selected from vegetable oils, e.g., safflower oil, cottonseed oil or maize (corn) oil.

Combinations containing two or more different permeation enhancers are likewise usable.

The term "antimicrcbial agent" is further to be understood as meaning in general agents suitable for preventing the growth of microbes in a pharmaceutical preparation, in particular in the liquid of the liquid-saturated carrier material of the present invention.

Examples of suitable antimicrobial agents include salts of chlorhexidine, such as iodopropynyl butylcarbamates, diazolidinylurea, chiorhexidine digluconate, chlorhexidine acetate, chlorhexidine isothionate or chlorhexidine hydrochloride. Other cationic antimicrobial agents are likewise usable, for example benzalkonium chloride, benzethonium chloride, triclocarbon, polyhexamethylenebiguanide, cetylpyridinium chloride, methylbenzethonium chloride.

Other antimicrobial agents include halogenated phenolic compounds, such as 2,4,4'-trichloro-2-hydroxydiphenyl ether (triclosan), parachiorometa xylenol (PCMX), methyl para-hydroxybenzoate and short-chain alcohols, such as ethanol, propanol and the like. The overall concentration of antimicrobial agents is preferably in the range from 0.01 to 2 wt %, based on the overall weight of the liquid in which it is present. Suitable carrier materials may be fiberplies, wovens, knits other than weft knits produced with independently-movable needles, sponges, sponge cloth, knit-stitched fibrous nonwoven web or felted-woven fabrics or feltlike materials etc.

The present invention further provides the method of using the above-described system as an integral constituent part of an iontophoretic patch, preferably as the anodic reservoir of the patch.

Example

Figure 1:
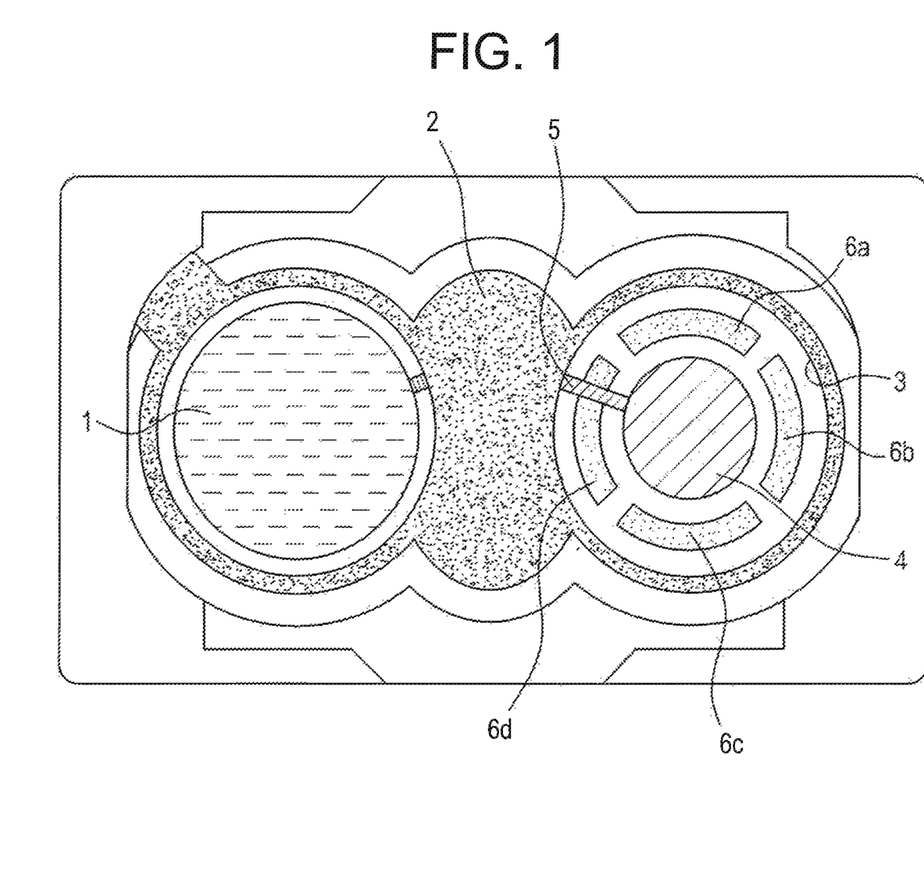
FIG. 1 illustrates in schematic form an inventive TTS as viewed from below.
Figure 2:
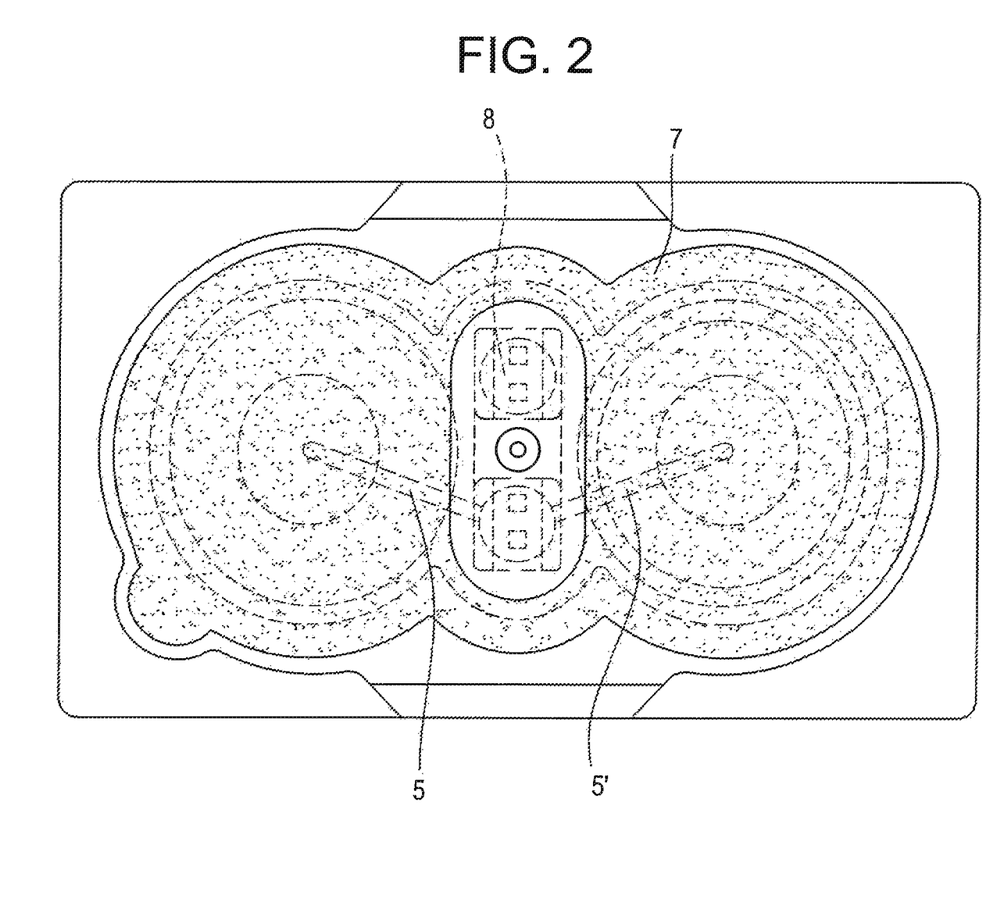
FIG. 2 illustrates in schematic form an inventive TTS as viewed from above.

The invention and its effectiveness will now be illustrated by way of example with reference to the accompanying drawings, where FIG. 1 shows in schematic form an invention TTS from below, i.e., from the skin side;

FIG. 2 shows in schematic form an invention TTS from above, i.e., from the skin-remote side;

FIGS. 3a, 3b, 3c and 3d show in schematic form, in component steps, how the active-containing carrier material is removed from its separately stored package and secured to the backing layer of the TTS.

FIG. 1 shows at 1 the active-containing carrier material which has a round shape and which has already been brought into position on the left-hand area of the TTS, while a covering film 2 having an opening 3 on the right-hand side gives a view of the electrode 4, the electrical in-line 5 and four arcuately shaped hook and loop tapes 6a, 6b, 6c and 6d. A further active-containing carrier material (not depicted) is then, in the next step, pressed onto the hook and loop tapes 6a, 6b, 6c and 6d and firmly secured with the hook and loop tapes 6a, 6b, 6c and 6d.

FIG. 2 shows essentially the backing layer 7 wherethrough the current supplies 5 and 5' are visible at left and at right, respectively. The current supply unit 8 with battery and electronic controls can be seen in the center of the depiction.

Figure 3A:
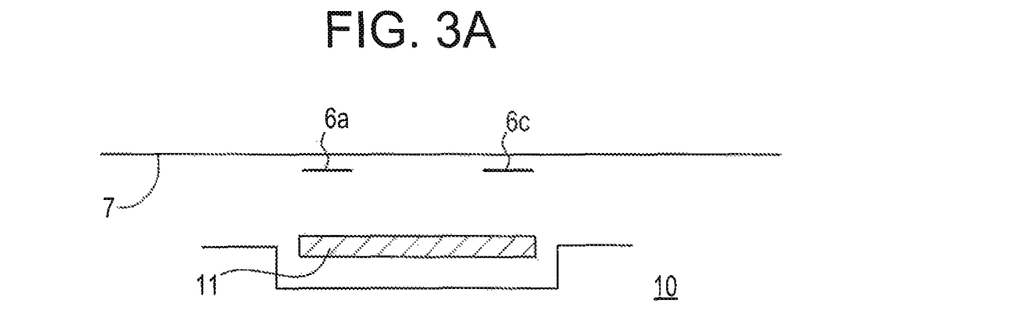
FIG. 3a illustrates in schematic form, the active-containing carrier material lying in an upwardly opened package that is disposed below hook and loop tape segments on a backing layer.

FIG. 3a shows at the top the backing layer 7 whereon are disposed two hook and loop tape segments 6a and 6c and at the bottom the active-containing carrier material 11 lying in an upwardly opened package 10 opened by a closure film being peeled off beforehand (not depicted).

Figure 3B:
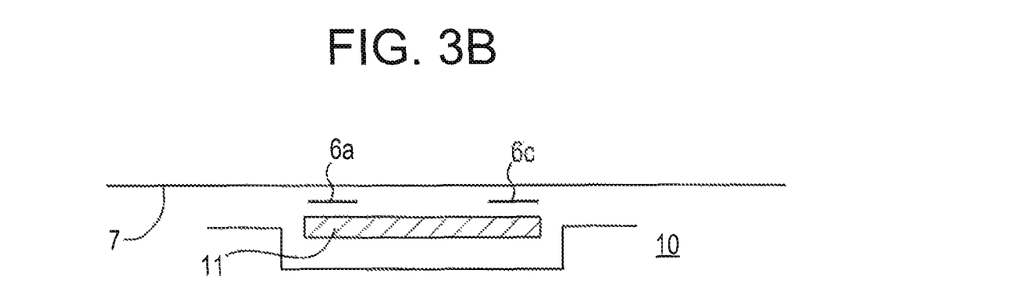
FIG. 3b illustrates in schematic form approximating the active-containing carrier material together with the backing layer and the hook and loop tape segments.

FIG. 3b shows how the active-containing carrier material 11 while still in the opened package 10 has been approximated together therewith to the backing layer 7 and the hook and loop tape segments 6a and 6c.

Figure 3C:
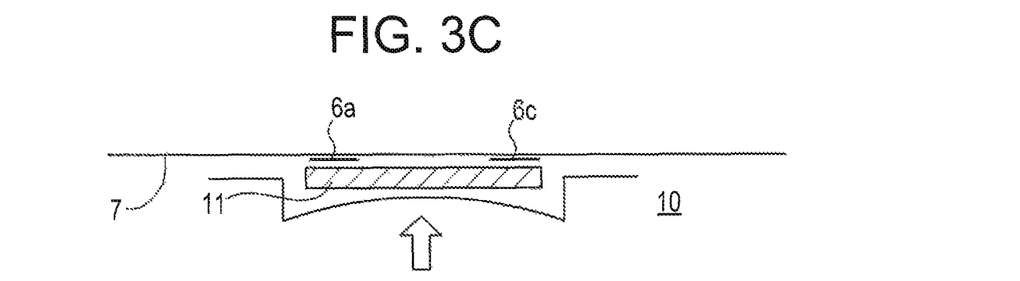
FIG. 3c illustrates in schematic form the pressing of the active-containing carrier material against the hook and loop tape segments and backing layer.

FIG. 3c shows how the active-containing carrier material 11 together with the package 10 is pressed from below in the arrow direction against the hook and loop tape segments 6a and 6c and against the backing layer 7.

Figure 3D:
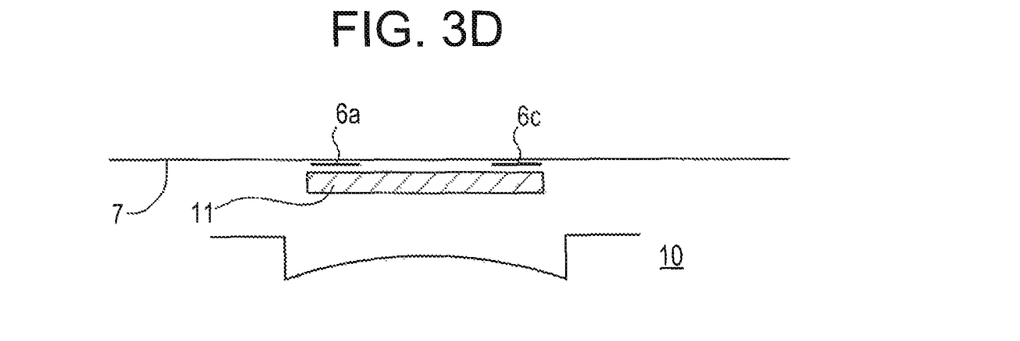
FIG. 3d illustrates in schematic form the securing of the active-containing carrier material to the hook and loop tape segments and hence the backing layer.

FIG. 3*d* shows how the package 10 is removed downwardly while the active-containing carrier material 11 remains secured to the hook and loop tape segments 6*a* and 6*c* and hence to the backing layer 7.

What is claimed is:

1. A method of attaching an active-containing carrier material to a TTS backing layer in the presence of hook and loop tape segments, wherein the active-containing carrier material is liquid saturated and the method comprises
   opening an upward side of a package containing the active-containing carrier material by removing a closure film from the package;
   approximating the active-containing carrier material in the opened package to the backing layer and the hook and loop tape segments disposed thereon,
   then pressing the package together with the active-containing carrier material present therein against the hook and loop tape segments on the backing layer,
   thereafter releasing and removing the package and leaving the active-containing carrier material secured to the hook and loop tape segments and to the backing layer.

* * * * *